US012606869B2

(12) United States Patent
Wolfgang et al.

(10) Patent No.: US 12,606,869 B2
(45) Date of Patent: Apr. 21, 2026

(54) METHODS FOR THE ADMINISTRATION OF ILOPERIDONE

(71) Applicant: Vanda Pharmaceuticals Inc., Washington, DC (US)

(72) Inventors: Curt Wolfgang, Germantown, MD (US); Mihael Polymeropoulos, Potomac, MD (US); Christian Lavedan, Potomac, MD (US); Simona Volpi, Derwood, MD (US)

(73) Assignee: Vanda Pharmaceutials Inc., Washington, DC (US)

( * ) Notice: Subject to any disclaimer, the term of this patent is extended or adjusted under 35 U.S.C. 154(b) by 742 days.

(21) Appl. No.: 17/716,968

(22) Filed: Apr. 8, 2022

(65) Prior Publication Data

US 2022/0259660 A1 Aug. 18, 2022

Related U.S. Application Data

(63) Continuation of application No. 16/406,229, filed on May 8, 2019, now abandoned, which is a continuation of application No. 14/847,784, filed on Sep. 8, 2015, now abandoned, which is a continuation of application No. 14/044,183, filed on Oct. 2, 2013, now abandoned, which is a continuation of application No. 12/208,027, filed on Sep. 10, 2008, now abandoned.

(51) Int. Cl.

| | |
|---|---|
| *C12Q 1/6883* | (2018.01) |
| *A61K 31/135* | (2006.01) |
| *A61K 31/4525* | (2006.01) |
| *A61K 31/454* | (2006.01) |
| *A61K 31/496* | (2006.01) |
| *A61P 25/18* | (2006.01) |

(52) U.S. Cl.
CPC .......... *C12Q 1/6883* (2013.01); *A61K 31/135* (2013.01); *A61K 31/4525* (2013.01); *A61K 31/454* (2013.01); *A61K 31/496* (2013.01); *A61P 25/18* (2018.01); *C12Q 2600/106* (2013.01); *C12Q 2600/156* (2013.01)

(58) Field of Classification Search
CPC ........... C12Q 1/6883; C12Q 2600/106; C12Q 2600/156; A61P 25/18; A61K 31/135; A61K 31/4525; A61K 31/454; A61K 31/496
See application file for complete search history.

(56) References Cited

U.S. PATENT DOCUMENTS

| | | | |
|---|---|---|---|
| 4,965,188 | A | 10/1990 | Mullis et al. |
| 5,130,238 | A | 7/1992 | Malek et al. |
| 5,364,866 | A | 11/1994 | Strupczewski et al. |
| 5,846,717 | A | 12/1998 | Brow et al. |
| 5,981,174 | A | 11/1999 | Wolf et al. |
| 6,001,567 | A | 12/1999 | Brow et al. |
| 7,179,597 | B2 | 2/2007 | Woosley |
| 7,767,230 | B2 | 8/2010 | Ahlheim et al. |
| 7,799,782 | B2 | 9/2010 | Munson et al. |
| 7,977,356 | B2 | 7/2011 | Grimler et al. |
| 8,314,129 | B2 | 11/2012 | Grimler et al. |
| 8,460,867 | B2 | 6/2013 | Kudaravalli et al. |
| 8,586,610 | B2 * | 11/2013 | Wolfgang ............ A61K 31/454 |
| | | | 514/320 |
| 8,652,776 | B2 | 2/2014 | Lavedan et al. |
| 8,999,638 | B2 | 4/2015 | Wolfgang et al. |
| 9,057,104 | B2 | 6/2015 | Lavedan et al. |
| 9,072,742 | B2 | 7/2015 | Lavedan et al. |
| 9,074,254 | B2 | 7/2015 | Lavedan et al. |
| 9,074,255 | B2 | 7/2015 | Lavedan et al. |
| 9,074,256 | B2 | 7/2015 | Lavedan et al. |
| 9,080,214 | B2 | 7/2015 | Lavedan et al. |
| 9,138,432 | B2 | 9/2015 | Wolfgang et al. |
| 9,157,121 | B2 | 10/2015 | Wolfgang et al. |
| 9,243,295 | B2 | 1/2016 | Lavedan et al. |
| 9,328,387 | B2 | 5/2016 | Lavedan et al. |
| 9,408,839 | B2 | 8/2016 | Lavedan et al. |
| 10,272,076 | B2 * | 4/2019 | Wolfgang ............ A61K 31/454 |
| 10,563,259 | B2 | 2/2020 | Wolfgang et al. |
| 10,563,260 | B2 | 2/2020 | Lavedan et al. |
| 10,563,261 | B2 | 2/2020 | Lavedan et al. |
| 10,570,452 | B2 | 2/2020 | Lavedan et al. |
| 10,570,453 | B2 | 2/2020 | Lavedan et al. |
| 10,874,659 | B2 | 12/2020 | Phadke et al. |
| 11,071,728 | B2 | 7/2021 | Polymeropoulos |
| 11,214,827 | B2 | 1/2022 | Polymeropoulos et al. |
| 11,607,408 | B2 | 3/2023 | Smieszek et al. |

(Continued)

FOREIGN PATENT DOCUMENTS

| | | |
|---|---|---|
| WO | 0055624 A2 | 9/2000 |
| WO | 0149883 A2 | 7/2001 |

(Continued)

OTHER PUBLICATIONS

Jain, K.K. Expert Opinion on Investigational Drugs 9(12):2935-2943. (Year: 2000).*
L. Bertilsson et al., Molecular Genetics of CYP2D6: Clinical Relevance with Focus on Psychotropic Drugs, Br. J. Clin. Pharmacol. 53(2): 111-122 (2002).
Janssen Pharmaceutica Products, L.P., Risperdal® (Risperidone) tablets/oral solution; Risperdal® M-TAB™ (Risperidone) Orally Disintegrating Tablets Aug. 2007 Label, available at https://www.accessdata.fda.gov/drugsatfda_docs/label/2007/020272s46s47,20588s36s37,21444s20s21lbl.pdf (last visited Sep. 11, 2025), pp. 28, 37-38 (Aug. 2007), 48 pages.
Vanda Pharmaceuticals Inc., Fanapt Full Prescribing Information, Apr. 2024 Revision, available at https://fanaptpro.com/wp-content/uploads/Fanapt-Prescribing-Information.pdf (last visited Sep. 11, 2025), § 2.2 (Apr. 2024), 33 pages.

(Continued)

*Primary Examiner* — Diana B Johannsen
(74) *Attorney, Agent, or Firm* — Hoffman Warnick LLC

(57) ABSTRACT

The present invention relates to methods for the identification of genetic polymorphisms that may be associated with a risk for QT prolongation after treatment with iloperidone and related methods of administering iloperidone to patients with such polymorphisms.

20 Claims, No Drawings

Specification includes a Sequence Listing.

(56) References Cited

U.S. PATENT DOCUMENTS

| | | | |
|---|---|---|---|
| 11,723,903 | B2 | 8/2023 | Polymeropoulos |
| 12,146,185 | B2 | 11/2024 | Polymeropoulos et al. |
| 2001/0034023 | A1 | 10/2001 | Stanton, Jr. et al. |
| 2002/0022054 | A1 | 2/2002 | Sawada et al. |
| 2002/0127561 | A1 | 9/2002 | Bee et al. |
| 2003/0083485 | A1 | 5/2003 | Milos et al. |
| 2003/0144220 | A1* | 7/2003 | Obach ............... A61K 31/4745 |
| | | | 514/249 |
| 2003/0170176 | A1 | 9/2003 | Leyland-Jones |
| 2004/0072235 | A1 | 4/2004 | Dawson |
| 2004/0091909 | A1 | 5/2004 | Huang |
| 2004/0096874 | A1 | 5/2004 | Neville et al. |
| 2004/0133352 | A1 | 7/2004 | Bevilacqua et al. |
| 2005/0032070 | A1* | 2/2005 | Raimundo ............. C07H 21/04 |
| | | | 435/325 |
| 2008/0166357 | A1 | 7/2008 | Gotz et al. |
| 2022/0259660 | A1* | 8/2022 | Wolfgang ............... A61P 25/18 |
| 2023/0330078 | A1* | 10/2023 | Wolfgang ............... A61P 25/18 |

FOREIGN PATENT DOCUMENTS

| | | | |
|---|---|---|---|
| WO | 0179554 | A1 | 10/2001 |
| WO | WO2001079554 | A1 * | 10/2001 |
| WO | 0244994 | A2 | 6/2002 |
| WO | 0250283 | A2 | 6/2002 |
| WO | 02064141 | A1 | 8/2002 |
| WO | 02099118 | A2 | 12/2002 |
| WO | 03017946 | A2 | 3/2003 |
| WO | 03038123 | A2 | 5/2003 |
| WO | 03054226 | A3 | 7/2003 |
| WO | 2004006886 | A2 | 1/2004 |
| WO | 2004009760 | A2 | 1/2004 |
| WO | 2004074456 | | 9/2004 |

OTHER PUBLICATIONS

Decision Denying Institution of Inter Partes Review, *Roxane Laboratories, Inc.* v. *Vanda Pharmaceuticals Inc.*, case PR2016-00690, Patent 9, 138,432, entered Aug. 30, 2016, 24 pages.
U.S. Department of Health and Human Services, Food and Drug Administration ("FDA"), Guidance for Industry, In Vivo Drug Metabolism/Drug Interaction Studies—Study Design, Data Analysis, and Recommendations for Dosing and Labeling (Nov. 1999) (available at http://www.fda.gov/OHRMS/DOCKETS/98fr/994718gd. pdf) (accessed Feb. 22, 2016), 19 pages.
K. Brøsen, Differences in Interactions of SSRIs, Int. Clin. Psychopharmacol. Supp. 5:S45-47 (Sep. 1998).
N.E. Mealy et al., Annual Review 2002: Psychopharmacologic Drugs, Drugs of the Future 27(10):995-1027 (Oct. 2002).
U.S. Department of Health and Human Services, Food and Drug Administration ("FDA"), Guidance for Industry, Drug Metabolism/ Drug Interaction Studies in the Drug Development Process: Studies In Vitro (Apr. 1997) (available at http:/www.fda.gov/downloads/ AboutFDA/CentersOffices/CDER/UCM142439.pdf) (accessed Feb. 22, 2016), 13 pages.
R.R. Shah, Pharmacogenetic Aspects of Drug-Induced Torsade de Pointes: Potential Tool for Improving Clinical Drug Development and Prescribing, Drug Safety 27(3):145-72 (Mar. 2004).
J. Kirchheiner et al., CYP2D6 and CYP2C19 Genotype-Based Dose Recommendations for Antidepressants: A First Step Towards Sub-population-Specific Dosages, Acta Psychiatrica Scandinavica 104(3):173-92 (Sep. 2001).
M.A. Raggi et al., Atypical Antipsychotics: Pharmacokinetics, Therapeutic Drug Monitoring and Pharmacological Interactions, Current Med. Chem. 11(3):279-96 (Feb. 2004).
Linda M. Distlerath et al., Purification and Characterization of the Human Liver Cytochromes P-450 Involved in Debrisoquine 4-Hydroxylation and Phenacetin O-Deethylation, Two Prototypes for Genetic Polymorphism in Oxidative Drug Metabolism, J. Biol. Chem. 260(15):9057-9067 (1985).

Tsutomu Shimada et al., Human Liver Microsomal Cytochrome P-450 Mephenytoin 4-Hydroxylase, a Prototype of Genetic Polymorphism in Oxidative Drug Metabolism, J. Biol. Chem. 261(2):909-921 (Feb. 1986).
F. Peter Guengerich et al., Characterization of Rat and Human Liver Microsomal Cytochrome P-450 Forms Involved in Nifedipine Oxidation, a Prototype for Genetic Polymorphism in Oxidative Drug Metabolism, J. Biol. Chem. 261 (11):5051-5061 (1986).
Rajendrani Mukhopadhyay, Human Cytochrome P450s: The Work of Frederick Peter Guengerich, J. Biol. Chem. 287(19):15798-15800 (May 2012).
F. Peter Guengerich et al., Diversity in the Oxidation of Substrates by Cytochrome P450 2D6: Lack of an Obligatory Role of Aspartate 301—Substrate Electrostatic Bonding, Biochemistry 41(36):11025-11034 (2002).
A.E. Mutlib et al., Application of hyphenated LC/NMR and LC/MS techniques in rapid identification of in vitro and in vivo metabolites of iloperidone, Drug Metab. Dispos. 23(9):951-964 (1995).
US FDA, NDA 22-192 (FANAPT® (iloperidone)), Clinical Pharmacology and Biopharmaceutics Review(s), 45 pages (Sep. 27, 2007 and Nov. 6, 2008).
J. Kirchheiner et al., Pharmacogenetics of antidepressants and antipsychotics: the contribution of allelic variations to the phenotype of drug response, Mol. Psychiatry 9:442-473 (2004).
Werner Steimer & Julia M. Potter, Pharmacogenetic screening and therapeutic drugs, Clin. Chim. Acta 315(1-2):137-155 (2002).
K. Probst-Schendzielorz et al., Effect of Cytochrome P450 polymorphism on the action and metabolism of selective serotonin reuptake inhibitors, Expert Opin. Drug Metab. Toxicol. 11(8):1219-1232 (2015).
Paul Rowland et al., Crystal Structure of Human Cytochrome P450 2D6, J. Biol. Chem. 281(11):7614-7622 (2006).
Jürgen Brockmöller et al., The impact of the CYP2D6 polymorphism on haloperidol pharmacokinetics and on the outcome of haloperidol treatment, Clin. Pharmacol. Ther. 72(4):438-452 (2002).
Adrián Llerena et al., "QTc internal lengthening is related to CYP2D6 hydroxylation capacity and plasma concentration of thioridazine in patients," J. Psychopharmacol. 16(4):361-364 (2002).
R. Thanacoody et al., Influence of CYP2D6 genotype on the QTc interval and plasma concentrations of thioridazine and its metabolites in psychiatric patients taking chronic therapy, Clin. Pharmacol. Ther. 73(2):P77 (2003).
M. Desai et al., Pharmacokinetics and QT interval pharmacodynamics of oral haloperidol in poor and extensive metabolizers of CYP2D6, Pharmacogenomics J. 3:105-113 (2003).
Novartis Clinical Study Report, Study No. CILO522 0104, "An open-label study to characterize the pharmacokinetics of iloperidone in poor and extensive 2D6 metabolizers and to evaluate the interaction of iloperidone with a cytochrome P450 2D6 prototype substrate (dextromethorphan) in healthy subjects" (2002), 53 pages.
US FDA, NDA 22-192 (FANAPT® (iloperidone)), Pharmacology Review, pp. 1-44 of 89 pages, review submitted to Division File System Jun. 30, 2008.
US FDA, NDA 22-192 (FANAPT® (iloperidone)), Pharmacology Review, pp. 45-89 of 89 pages, review submitted to Division File System Jun. 30, 2008.
Vanda, Study No. VP-VYV-683-3101, "Treatment-Emergent Adverse Events: By Treatment and Body System" (2007), 2 pages.
Urs A. Meyer, Pharmacogenetics and adverse drug reactions, Lancet 356:1667-1671 (2000).
Daniel C. Liebler & F. Peter Guengerich, Elucidating Mechanisms of Drug-Induced Toxicity, Nature Rev. Drug Discovery 4:410-420 (2005).
Raimundo et al., A novel intronic mutation 2988G>A, with high predictivity for impaired function of cytochrome P450 2D6 in white subjects, Clinical Pharmacology & Therapeutics 76(2):128-138 (2004).
A. Gaedigk et al., Deletion of the Entire Cytochrome P450 CYP2D6 Gene as a Cause of Impaired Drug Metabolism in Poor Metabolizers of the Debrisoquine/Sparteine Polymorphism, Am. J. Hum. Drug Genet. 48(5):943-950 (1991).

(56) References Cited

OTHER PUBLICATIONS

J. Stingl & R. Viviani, Polymorphism in CYP2D6 and CYP2C19, members of the cytochrome P450 mixed-function oxidase system, in the metabolism of psychotropic drugs, J. Intern. Med. 277:167-177 (2015).

F. Peter Guengerich, Role of Cytochrome P450 Enzymes in Drug-Drug Interactions, Adv. in Pharmacol. 43:7-35 (1997).

Novartis Pharmaceuticals Corporation, FANAPT® (iloperidone) Label (2014), 20 pages.

Novartis Clinical Study Report, Study No. CILO522 2328, "A randomized, open-label, multicenter, 5-arm, safety study evaluating the effect of oral iloperidone at doses of 8 mg b.i.d., 12 mg b.i.d., and 24 mg q.d. on QTc interval duration in the presence and absence of metabolic inhibition, relative to other antipsychotics (ziprasidone 80 mg b.i.d, and quetiapine 375 mg b.i.d., in the presence and absence of metabolic inhibition), in otherwise healthy patients diagnosed with schizophrenia or schizoaffective disorder" (2002); pp. 1-51 of 90.

Novartis Clinical Study Report, Study No. CILO522 2328, "A randomized, open-label, multicenter, 5-arm, safety study evaluating the effect of oral iloperidone at doses of 8 mg b.i.d., 12 mg b.i.d., and 24 mg q.d. on QTc interval duration in the presence and absence of metabolic inhibition, relative to other antipsychotics (ziprasidone 80 mg b.i.d, and quetiapine 375 mg b.i.d., in the presence and absence of metabolic inhibition), in otherwise healthy patients diagnosed with schizophrenia or schizoaffective disorder" (2002); pp. 52-90 of 90.

Novartis Pharmacogenetics Report, Protocol No. CILO522 2328, Study No. PGR-39, "Pharmacogenetics study of CYP2D6 polymorphisms on iloperidone concentration in study ILO522A 2328" 13 pages.

Vanda Pharmacogenetics Report, Study No. CILO522 2328-PG-1, "CILO522 2328 PG Report: Single Nucleotide Polymorphisms in the CYP2D6 Gene are Correlated with Iloperidone Drug Exposure Levels Impacting the Degree of QTc Prolongation Associated with Iloperidone Treatment" (2006), 10 pages.

Patent Cooperation Treaty, International Search Report and the Written Opinion of the International Searching Authority International Application No. PCT/US2009/056517, 18 pages (Nov. 27, 2009).

Caccia, New Antipsychotic Agents for Schizophrenia: Pharmacokinetics and Metabolism Update, Current Opinion in Investigational Drugs, 3(7):1073-1080 (Jul. 2002).

Bradford, CYP2D6 Allele Frequency in European Caucasians, Asians, Africans and Their Descendants, Pharmacogenomics 3(2):229-243 (2002).

S. Chainuvati et al., Combined Phenotypic Assessment of Cytochrome p450, 1A2, 2C9, 2C19, 2D6, and 3A, N-acetyltransferase-2 and Xanthine Oxidase Activities with the "Cooperstown 5+1 Cocktail", Clinical Pharmacol. Ther., 74(5):437-47 (Nov. 2003).

M. L. Dahl et al., Genetic Analysis of the CYP2D Locus in Relation to Debrisoquine Hydroxylation Capacity in Korean, Japanese, and Chinese Subjects, Pharmacogenetics, 5(3):159-164 (1995).

A. C. Gough et al., Identification of the Primary Gene Defect at the Cytochrome P 450 CYP2D Locus, Nature, 347:773-776 (Oct. 25, 1990).

N. Hanioka et al., The Human CYP2D Locus Associated with a Common Genetic Defect in Durg Oxidation: A G1934—A Base Change in Intron 3 of a Mutant CYP2D6 Allele Results in an Aberrant 3' Splice Recognition Site, Am. J. Hum. Genet., 47(6):994-1001 (1990).

P. Jaanson et al., Maintenance Therapy with Zuclopenthixol Decanoate: Associations Between Plasma Concentrations, Neurological Side Effects and CYP2D6 Genotype, Psychopharmacology, 162:67-73 (2002).

K. K. Jain, An assessment of iloperidone for the treatment of schizophrenia, Expert Opin. Investig. Drugs, 9(12):2935-2943 (Dec. 2000).

I. Johansson et al., Genetic Analysis of the Chinese Cytochrome P4502D Locus: Characterization of Variant CYP2D6 Genes Present In Subjects with Diminished Capacity for Debrisoquine Hydroxylation, Molecular Pharmacology, 46:452-459 (1994).

M. Kagimoto et al., Multiple Mutations of the Human Cytochrome P45011D6 Gene (CYP2D6) In Poor Metabolizers of Debrisoquine, The Journal of Biological Chemistry, 265(28):17209-17214 (1990).

J. P. Kelleher et al., Advances in Atypical Antipsychotics for the Treatment of Schizophrenia: New Formulations and New Agents, CNS Drugs, 16(4):249-261 (2002).

V. Lyamichev et al., Polymorphism Identification and Quantitative Detection of Genomic DNA by Invasive Cleavage of Oligonucleotide Probes, Nat. Biotechnol., 17(3):292-296 (Mar. 1999).

S. McElroy et al., CYP2D6 Genotyping as an Alternative to Phenotyping for Determination of Metabolic Status in a Clinical Trial Setting, AAPS PharmSci, 2(4):1-11 (Oct. 29, 2000).

A. E. Mutlib et al., Application of Liquid Chromatography/Mass Spectrometry in Accelerating the Identification of Human Liver Cytochrome P450 isoforms Involved in the Metabolism of iloperidone, J. Pharmacol. Exper. Ther., 286 (3):1285-1293 (1998).

M. Nevilie et al., Characterization of Cytochrome P450 2D6 Alleles Using the Invader System, BioTechniques, Suppl:34-8, 40-3 (Jun. 2002).

N. Subramanian et al., Receptor Profile of P88-8991 and P95-12133, Metabolites of the Novel Antipsychotic Iloperidone, Prog. Neuropsychopharmacol. Biol. Psychiatry, 26(3):553-560 (2002).

H. Yokota et al., Evidence for a New Variant CYP2D6 Allele CYP2D6J in a Japanese Population Associated with Lower In Vivo Rates of Sparteine Metabolism, Pharmacogenetics, 3(5):256-263 (1993).

Home p. of the Human Cytochrome P450 (CYP) Allele Nomenclature Committee, (www. cypalleles.ki.se/) (May 2008).

R. P. Sheridan et al., Empirical Regioselectivity Models for Human Cytochromes P450 3M, 2D6, and 2C9, J. Med. Chem. 50(14): 3173-3184 (Jun. 2007).

D. Ryan et al., Non-PCR-Dependent Detection of the Factor V Leiden Mutation From Genomic DNA Using a Homogeneous Invader Microtiter Plate Assay, Mol. Diagn., 4(2):135-144 (1999).

T. Shimada et al., Characterization of (+/−)-Bufuralol Hydroxylation Activities in Liver Microsomes of Japanese and Caucasian Subjects Genotyped for CYP2D6, Pharmacogenetics 11(2):143-156 (2001).

S. Fuselli et al., Molecular diversity at the CYP2D6 locus in the Mediterranean region, Eur. J. Hum. Genet., 12(11):916-924 (Nov. 2004).

C. Sachse et al., Cytochrome P450 2D6 in a Caucasian Population: Allele Frequencies and Phenotypic Consequences, Am. J. Hum. Genet., 60(2):284-295 (Feb. 1997).

S. L. Wang et al., G169R Mutation Diminishes the Metabolic Activity of CYP2D6 in Chinese, Drug Metab. Dispos., 27(3):385-388 (Mar. 1999).

S. M. Sainati, Safety, Tolerability, and Effect of Food on the Pharmacokinetics of Iloperidone (HP 873), a Potential Atypical Antipsychotic, J. Clin. Pharmacol. 35(7):713-720 (1995).

C. L. Alfaro et al., CYP2D6 inhibition by fluoxetine, paroxetine, sertraline, and venlafaxine in a crossover study: intraindividual variability and plasma concentration correlations, J Clin Pharmacol. 40(1):58-66 (2000).

S. M. Cheer et al., Fluoxetine: a review of its therapeutic potential in the treatment of depression associated with physical illness, Drugs 61(1):81-110 (2001).

Novartis Pharmaceuticals Corporation, Fanapt Full Prescribing Information (20 pages) (Apr. 2014).

Vanda Pharmaceuticals Inc., Fanapt (iloperidone) Tablets Full Prescribing Information (23 pages) (May 2009).

Janssen Pharmaceutica Products, LP, Risperdal (Risperidone) Tablets/ Oral Solution< Risperdal M-Tab™ (Risperidone) Orally Disintegrating Tablets Risperdal® (risperidone) Label (2003), 34 pages.

Dan M. Roden, Drug-induced prolongation of the QT interval, N Engl J Med. 350(10):1013-22 (2004).

*Vanda Pharm. Inc. v. West-Ward Pharm Int'l Ltd*, 887 F.3d 1117 (Fed. Cir. 2018).

* cited by examiner

METHODS FOR THE ADMINISTRATION OF ILOPERIDONE

CROSS-REFERENCE TO RELATED APPLICATIONS

This application is a continuation of U.S. patent application Ser. No. 16/406,229, filed May 8, 2019 (now abandoned), which is a continuation of U.S. patent application Ser. No. 14/847,784, filed Sep. 8, 2015 (now abandoned), which is a continuation of U.S. patent application Ser. No. 14/044,183, filed Oct. 2, 2013 (now abandoned), which is a continuation of U.S. patent application Ser. No. 12/208,027, filed Sep. 10, 2008 (now abandoned). Each of the foregoing patent applications is incorporated herein as though fully set forth.

SEQUENCE LISTING

The sequence listing contained in the electronic file entitled "VAND-0002-US—CIP-CON4_SequenceListing.txt," created Apr. 7, 2022 and comprising 4 KB, is hereby incorporated herein by reference.

BACKGROUND OF THE INVENTION

Several genes associated with drug metabolism have been found to be polymorphic.

As a result, the abilities of individual patients to metabolize a particular drug may vary greatly. This can prove problematic or dangerous where an increased concentration of a non-metabolized drug or its metabolites is capable of producing unwanted physiological effects.

The cytochrome P450 2D6 gene (CYP2D6), located on chromosome 22, encodes the Phase I drug metabolizing enzyme debrisoquine hydroxylase. A large number of drugs are known to be metabolized by debrisoquine hydroxylase, including many common central nervous system and cardiovascular drugs. One such drug is iloperidone (1-[4-[3-[4-(6-fluoro-1,2-benzisoxazol-3-yl)-1-piperidinyl] propoxy]-3-methoxyphenyl]ethanone). Iloperidone and methods for its production and use as an antipsychotic and analgesic are described in U.S. Pat. No. 5,364,866 to Strupczewski et al. The diseases and disorders that can be treated by administration of iloperidone include all forms of schizophrenia (i.e., paranoid, catatonic, disorganized, undifferentiated, and residual), schizoaffective disorders, bipolar mania/depression, cardiac arrhythmias, Tourette's Syndrome, brief psychotic disorder, delusional disorder, psychotic disorder NOS (not otherwise specified), psychotic disorder due to a general medical condition, schizophreniform disorder, and substance-induced psychotic disorder. P88 is an active metabolite of iloperidone. See, e.g., PCT WO2003020707, which is incorporated herein by reference.

Among the unwanted physiological effects associated with an increased concentration of iloperidone or its metabolites is prolongation of the electrocardiographic QT interval. Mutations in the CYP2D6 gene have been associated with a number of drug metabolism-related phenotypes. These include the ultra rapid metabolizer (UM), extensive metabolizer (EM), intermediate metabolizer (IM), and poor metabolizer (PM) phenotypes. Where a particular drug is capable of producing unwanted physiological effects in its metabolized or non-metabolized forms, it is desirable to determine whether a patient is a poor metabolizer of the drug prior to its administration.

A number of references are directed toward the identification of CYP2D6 mutations and their corresponding phenotypes. For example, United States Patent Application Publication No. 2003/0083485 to Milos et al. describes a novel CYP2D6 variant associated with the PM phenotype and methods for assessing whether an individual possesses the variant prior to the administration of a drug. United States Patent Application Publication No. 2004/0072235 to Dawson describes a primer set useful in identifying variants of the CYP2D6 gene. Similarly, United States Patent Application Publication No. 2004/0091909 to Huang describes methods for screening an individual for variants in the CYP2D6 gene and other cytochrome P450 genes and tailoring the individual's drug therapy according to his or her phenotypic profile. Finally, United States Patent Application Publication No. 2004/0096874 to Neville et al. describes methods for identifying cytochrome P450 variants.

SUMMARY OF THE INVENTION

The present invention comprises the discovery that treatment of a patient, who has lower CYP2D6 activity than a normal person, with a drug that is pre-disposed to cause QT prolongation and is metabolized by the CYP2D6 enzyme, can be accomplishing more safely by administering a lower dose of the drug than would be administered to a person who has normal CYP2D6 enzyme activity. Such drugs include, for example, dolasetron, paroxetine, venlafaxin, and iloperidone. Patients who have lower than normal CYP2D6 activity are herein referred to as CYP2D6 Poor Metabolizers.

This invention also relates to methods for the identification of genetic polymorphisms that may be associated with a risk for QT prolongation after treatment with compounds metabolized by the CYP2D6 enzyme, particularly iloperidone or an active metabolite thereof or a pharmaceutically acceptable salt of either (including, e.g., solvates, polymorphs, hydrates, and stereoisomers thereof), and related methods of administering these compounds to individuals with such polymorphisms.

The present invention describes an association between genetic polymorphisms in the CYP2D6 locus, corresponding increases in the concentrations of iloperidone or its metabolites, and the effect of such increases in concentrations on corrected QT (QTc) duration relative to baseline. Any number of formulas may be employed to calculate the QTc, including, for example, the Fridericia formula (QTcF) and the Bazett formula (QTcB), among others. The present invention includes any such formula or method for calculating a QTc.

A first aspect of the invention provides a method for treating a patient with iloperidone or an active metabolite thereof or a pharmaceutically acceptable salt of either, comprising the steps of determining the patient's CYP2D6 genotype and administering to the patient an effective amount of iloperidone or an active metabolite thereof or a pharmaceutically acceptable salt of either based on the patient's CYP2D6 genotype, such that patients who are CYP2D6 poor metabolizers receive a lower dose than patients who are CYP2D6 normal metabolizers.

Another aspect of the invention provides a method for treating a patient who is a CYP2D6 poor metabolizer with iloperidone or an active metabolite thereof or a pharmaceutically acceptable salt of either, wherein the patient is administered a lower dosage than would be given to an individual who is not a CYP2D6 poor metabolizer.

Another aspect of the invention provides a method of treating a patient with iloperidone or an active metabolite thereof or a pharmaceutically acceptable salt of either comprising the steps of determining whether the patient is being administered a CYP2D6 inhibitor and reducing the dosage of drug if the patient is being administered a CYP2D6 inhibitor.

Another aspect of the invention provides a method for determining a patient's CYP2D6 phenotype comprising the steps of administering to the patient a quantity of iloperidone or an active metabolite thereof or a pharmaceutically acceptable salt of either, determining a first concentration of at least one of iloperidone and an iloperidone metabolite in the patient's blood, administering to the patient at least one CYP2D6 inhibitor, determining a second concentration of at least one of iloperidone and an iloperidone metabolite in the patient's blood, and comparing the first and second concentrations.

Another aspect of the invention provides a method for determining whether a patient is at risk for prolongation of his or her QTc interval due to iloperidone administration comprising the step of: determining a patient's CYP2D6 metabolizer status by either determining the patient's CYP2D6 genotype or CYP2D6 phenotype. In the case that a patient is determined to be at risk for prolongation of his or her QTc interval, the dose of iloperidone administered to the patient may be reduced.

Another aspect of the invention provides a method of administering iloperidone or an active metabolite thereof, or a pharmaceutically acceptable salt of either, for the treatment of a disease or disorder in a human patient comprising the steps of determining the activity of the patient's CYP2D6 enzyme on at least one of iloperidone and its metabolites relative to the activity of a wild type CYP2D6 enzyme and reducing the dose of at least one of iloperidone and its pharmaceutically acceptable salts if the patient's CYP2D6 enzyme activity is less than that of the wild type CYP2D6.

Another aspect of the invention relates to modifying the dose and/or frequency of dosing with iloperidone or a pharmaceutically acceptable salt thereof based on the P88: P95 ratio and/or the (P88+iloperidone):P95 ratio in a blood sample of a patient being treated with iloperidone or P88, especially patients susceptible to QT prolongation or to harmful effects associated with QT prolongation.

Another aspect of the invention provides a kit for use in determining a CYP2D6 genotype of an individual, comprising a detection device, a sampling device, and instructions for use of the kit.

Another aspect of the invention provides a kit for use in determining a CYP2D6 phenotype of an individual, comprising a detection device, a collection device, and instructions for use of the kit.

Another aspect of the invention provides a kit for use in determining at least one of a P88 to P95 ratio and a P88 and iloperidone to P95 ratio in an individual, comprising a detection device, a collection device, and instructions for use of the kit.

Yet another aspect of the invention provides a method for commercializing a pharmaceutical composition comprising at least one of iloperidone, a pharmaceutically acceptable salt of iloperidone, an active metabolite of iloperidone, and a pharmaceutically acceptable salt of an active metabolite of iloperidone, said method comprising: obtaining regulatory approval of the composition by providing data to a regulatory agency demonstrating that the composition is effective in treating humans when administered in accordance with instructions to determine whether or not a patient is a CYP2D6 poor metabolizer prior to determining what dose to administer to the patient; and disseminating information concerning the use of such composition in such manner to prescribers or patients or both.

The foregoing and other features of the invention will be apparent from the following more particular description of embodiments of the invention.

DETAILED DESCRIPTION OF THE INVENTION

Iloperidone is a benzisoxazole-piperidinyl derivative, currently in development for the treatment of CNS disorders. Data from placebo-controlled Phase III studies of iloperidone showed a Fridericia correction of QT duration (QTcF) increase of 0.1 to 8.5 msec at doses of 4-24 mg, when comparing a single ECG at baseline to a single ECG at endpoint. At lower doses of iloperidone (4 mg-16 mg) QTcF prolongation was minimal (0.1-5 msec). In the most recent study, a greater prolongation was observed when higher doses of iloperidone (20-24 mg/day) were studied. The mean change in the QTcF at doses 20-24 mg/day was 8.5 msec, and 4.6 msec in the 12-16 mg/day dose range in this study. These data suggest that treatment with iloperidone can be associated with prolongation of the QT interval similar to other drugs in this class, and that the effect may be dose sensitive in the clinical dose range.

The research leading to the present invention was designed to examine the effect of different doses of iloperidone relative to the effect of ziprasidone and quetiapine on QTc duration under carefully controlled conditions. To further evaluate the possible relationship between exposure to iloperidone and the comparators to QTc duration, reassessment after pharmacological inhibition of the principle metabolic pathways for each drug, under steady-state conditions, was also planned.

Example 1

Blood samples for pharmacogenetic analysis were collected at screening. Two polymorphisms previously associated with poor metabolizing status were genotyped in the CYP2D6 locus, and 251 genotypes were collected. The individual genotypes were studied for detection of association between genotype class and concentrations of iloperidone and its metabolites P88 and P95. The functional effect of the polymorphisms was also evaluated by analyzing the effect of the addition of the CYP2D6 inhibitor paroxetine on the concentrations of the parent drug and its metabolites.

The research leading to the present invention identified a significant association between CYP2D6 genotype and concentrations of P88 before the addition of inhibitors as well as the effect of this association on QTc prolongation.

Iloperidone is a substrate for two P450 enzymes; CYP2D6 and CYP3A4. Most metabolic clearance of iloperidone depends on these two enzymes. CYP2D6 catalyzes hydroxylation of the pendant acetyl group to form metabolite P94, which is converted to P95 after some additional reactions. Addition of the CYP2D6 inhibitor fluoxetine, along with iloperidone resulted in increases of the area under the curve (AUC) for iloperidone and P88 of 131% and 119% respectively. Addition of the CYP3A4 inhibitor ketoconazole in interaction studies resulted in a 38-58% increase in the concentrations of iloperidone and its main metabolites P88 and P95. P88 has a pharmacological profile including affinity for the HERG channel similar to that of iloperidone. P95 is less lipophilic and is dissimilar in its binding profile compared to iloperidone, including having very low affinity for the HERG channel. For these reasons P95 is regarded as being pharmacologically inactive.

The addition of metabolic inhibitors in this study therefore allowed for an evaluation of the effect of increasing blood-concentration of iloperidone and/or its metabolites on QT duration. More specifically, this study allowed for an evaluation of the effect of iloperidone on QTc before and risperidone group, 28 of 33 of the ziprazidone group, and 23 of 33 of the quetiapine group.

B. Genotyping

Genotypes for the CYP2D6G1846A polymorphism were ascertained for 123 of the 128 consenting individuals, while genotypes for the CYP2D6C100T polymorphism were identified for all 128 participants. Genotyping was performed on amplified DNA fragments. The CYP2D6 genomic region was amplified using a triplex PCR strategy (Neville 2002). In brief, primers used were:

```
Exons 1 & 2        SEQ. ID. 1, 2D6L1F1:    CTGGGCTGGGAGCAGCCTC
                   SEQ. ID. 2, 2D6L1R1:    CACTCGCTGGCCTGTTTCATGTC Exons 3, 4, 5 & 6  SEQ. ID. 3, 2D6L2F:     CTGGAATCCGGTGTCGAAGTGG
                   SEQ. ID. 4, 2D6L2R2:    CTCGGCCCCTGCACTGTTTC Exons 7, 8 & 9     SEQ. ID. 5, 2D6L3F:     GAGGCAAGAAGGAGTGTCAGGG
                   SEQ. ID. 6, 2D6L3R5B:   AGTCCTGTGGTGAGGTGACGAGG
``` after the addition of the CYP2D6 inhibitor, paroxetine, as well as before and after the addition of the CYP3A4 inhibitor, ketoconazole.

The CYP2D6 gene is highly polymorphic, with more than 70 allelic variants described so far. See, e.g., www.imm-.ki.se/CYPalleles/CYP2D6.htm. Most embodiments of the present invention concern the two most common polymorphisms within the CYP2D6 gene in Caucasian populations, CYP2D6G1846A and CYP2D6P34S (also referred to as CYP2D6C100T). These polymorphisms correspond to nucleotides 3465 and 1719, respectively, in GenBank sequence M33388.1 (GI:181303). The CYP2D6P34S/CYP2D6C100T polymorphism also corresponds to nucleotide 100 in GenBank mRNA sequence M20403.1 (GI:181349).

The CYP2D6G1846A polymorphism (known as the CYP2D6*4 alleles, encompassing *4A, *4B, *4C, *4D, *4E, *4F, *4G, *4H, *4J, *4K, and *4L) represents a G to A transition at the junction between intron 3 and exon 4, shifting the splice junction by one base pair, resulting in frameshift and premature termination of the protein (Kagimoto 1990, Gough 1990, Hanioka 1990). The CYP2D6P34S/CYP2D6C100T polymorphism (known as the CYP2D6*10 and CYP2D6*14 alleles) represents a C to T change that results in the substitution of a Proline at position 34 by Serine (Yokota 1993, Johansson 1994). Both of these polymorphisms have been associated with reduced enzymatic activity for different substrates (Johansson 1994, Dahl 1995, Jaanson 2002, see also review by Bertilsson 2002)

Methods

A. Samples 128 individuals consented to the pharmacogenetic study. Blood samples were collected according to the pharmacogenetics protocol and after the consent of patients. The DNA was extracted from whole blood by Covance using the PUREGENE DNA isolation kit (D-50K).

The 128 individuals that participated were a good representation of the total sample of 165 individuals that participated in the trial. 22 of 29 total were from the iloperidone 8 mg bid group, 30 of 34 were from the iloperidone 12 mg bid group, 22 of 31 from the 24 mg qd group, 3 of 5 of the Amplification was performed on 40-100 ng of genomic DNA using a GC-rich PCR kit (Roche Diagnostics, Mannheim, Germany) according to the manufacturer's recommendations. Thermocycling conditions were as follows: initial denaturation (3 min 95° C.), 10 cycles of 30s of denaturation (30s at 95° C.), annealing (30s at 66° C.), and extension, (60s at 72° C.) followed by 22 cycles: 30s at 95° C., 30s at 66° C., 60s+5s/cycle at 72° C. A final extension followed (7 min at 72° C.).

Third Wave Technologies, Inc (Madison, Wis.) developed the probe sets for genotyping. Genotyping was performed on PCR products using the Invader© assay (Lyamichev 1999) (Third Wave Technologies, Inc) according to the manufacturer's recommendations.

The genotypes of individuals distributed among the three iloperidone groups were not significantly different (Table 1A and 1B).

TABLE 1A

Genotype frequencies by iloperidone dose class for CYP2D6C100T

| Iloperidone dose group | Genotype | | | |
| --- | --- | --- | --- | --- |
| | CC | CT | TT | Total |
| Ilo 8 mg bid | 19[a] | 2 | 1 | 22 |
| Ilo 12 mg bid | 23 | 6 | 1 | 30 |
| Ilo 24 mg qd | 15 | 6 | 1 | 22 |
| Total | 57 | 14 | 3 | 74 |

[a]number of individuals

TABLE 1B

Genotype frequencies by iloperidone dose class for CYP2D6G1846A

| Iloperidone dose group | Genotype | | | |
| --- | --- | --- | --- | --- |
| | AA | AG | GG | Total |
| Ilo 8 mg bid | 0 | 3 | 17 | 20 |
| Ilo 12 mg bid | 1 | 6 | 23 | 30 |
| Ilo 24 mg qd | 1 | 5 | 15 | 21 |
| Total | 2 | 14 | 55 | 71 |

C. Statistical Analysis

The genotype effect of the two CYP2D6 polymorphisms on period 1 concentrations was evaluated using the following ANOVA model. Concentrations of iloperidone, P88, and P95 at Period 1, without inhibitor, at the time at which maximum blood concentration of the parent compound or metabolite was reached (Tmax) were used as the dependent variable, the genotypes of each polymorphism as classes and the treatment as a covariate. In order to adjust for treatment effects after the single dose of iloperidone, the 8 mg bid was coded as 8, the 12 mg bid as 12 and the 24 mg qd as 24.

The function of these polymorphisms on the degree of inhibition of the CYP2D6 enzyme was calculated from the ratio of concentrations of P88 and P95 in period 2, after the addition of the inhibitor of CYP2D6. The concentrations of iloperidone and/or its metabolites (e.g., P88 and P95) may be determined in period 1 and/or period 2 by any known or later-developed method or device, including titration.

Results and Discussion

In order to understand the functional significance of the two CYP2D6 polymorphisms on the activity of the enzyme, the association of the various genotypes with the relative concentrations of the metabolites P88 and P95 were examined. It is known that P88 is degraded by CYP2D6 and that CYP2D6 is involved in the synthesis of P95. The relative amounts of P88 and P95 would therefore be controlled by the activity of the CYP2D6 enzyme. The ratio of P88/P95 was calculated before inhibition in Period 1 and at the Tmax of the two metabolites, as well as the ratio of P88/P95 in Period 2 after the addition of the CYP2D6 inhibitor paroxetine. In individuals with the wild type enzyme the concentration of P88 is expected to increase in Period 2, while in the same period the concentration of P95 is expected to decline.

For Period 1 the mean P88/P95 ratio among the 91 iloperidone treated patients was equal to 1.0 with a range from 0.14 to 8.19. Among the same individuals for Period 2 the mean ratio was 2.4 with a range from 0.5 to 8.49. The mean ratio of the ratios Period 1/Period 2 was equal to 0.37 with a range from 0.11 to 2.75.

Among the genotyped individuals the values were similar with means of 1; 2.45; and 0.37 for Period 1, Period 2, and Period 1/Period 2 respectively, indicating no sample bias. For polymorphism CYP2D6G1846A the means were significantly different between the three-genotype classes AA, AG and GG. For AA the respective values were 6.1, 3.41, and 1.89; for AG they were 2.4, 4.2, and 0.52; and for GG, 0.57, 1.94, and 0.28 (Table 2).

TABLE 2

| | Ratios of P88, P95 concentrations according to genotype | | |
|---|---|---|---|
| Population | P88/P95 Period 1 | P88/P95 Period 2 | P88/P95 (Period 1/Period 2) |
| All | 1.0 (0.14-8.19) | 2.45 (0.50-8.49) | 0.37 (0.11-2.75) |
| | | CYP2D6G1846A | |
| AA | 6.1 (3.96-8.19) | 3.41 (2.96-3.87) | 1.89 (1.0-2.75) |
| AG | 2.4 (0.44-7.0) | 4.20 (2.2-7.57) | 0.52 (0.14-1.28) |
| GG | 0.57 (0.14-2.2) | 1.94 (0.52-4.71) | 0.28 (0.11-0.61) |

The differences between genotype classes were significant at the p<0.0001 level in ANOVA test. These data suggest that the AA class represent a CYP2D6 poor metabolizer as indicated by the high ratio of P88/P95 in period 1 and the relatively small effect of the addition of the inhibitor in Period 2. The AG class seems to exhibit an intermediate phenotype between the poor metabolizer and the wild type with an approximately 2-fold reduction of the CYP2D6 activity after the addition of the inhibitor, as indicated by the ratio of the ratios (Table 2). This analysis provides a phenotypic characterization of the CYP2D6G1846A polymorphism as it relates to the metabolism of iloperidone.

Having established a functional role of this polymorphism, the concentrations of P88 at Period 1 at the Tmax of P88 were calculated for each genotype class. P88 concentrations were significantly (p<0.005) higher for the AA and AG classes as compared to the GG class for each of the three iloperidone dose groups (Table 3).

TABLE 3

| P88 concentrations in Period 1 according to CYP2D6 genotype | | | |
|---|---|---|---|
| Genotype | N obs | LSMeans | P value |
| AA | 2 | 62.70 | <0.0001 |
| AG | 14 | 31.40 | |
| GG | 55 | 21.03 | |
| | TRT dose | | 0.0015 |
| | CYP2D6G1846A *TRT dose | | 0.0058 |

Although the number of individuals carrying the A allele is limited, the results obtained in the study consistently suggest that individuals of the AA and AG class are expected to experience higher concentrations of P88 at Tmax as compared with GG individuals. Similar results were obtained with polymorphism CYP2D6C100T (Table 4 and 5).

TABLE 4

| | Ratios of P88, P95 concentrations according to genotype | | |
|---|---|---|---|
| Population | P88/P95 Period 1 | P88/P95 Period 2 | P88/P95 (Period 1/Period 2) |
| All | 1.0 (0.14-8.19) | 2.45 (0.50-8.49) | 0.37 (0.11-2.75) |
| | | CYP2D6C100T | |
| CC | 0.6 (0.14-2.28) | 1.93 (0.52-4.71) | 0.27 (0.11-0.61) |
| CT | 2.2 (0.44-7.0) | 4.14 (2.2-7.57) | 0.49 (0.14-1.28) |
| TT | 5.24 (3.56-8.19) | 4.19 (2.96-5.74) | 1.46 (0.62-2.75) |

TABLE 5

| P88 concentrations in Period 1 according to CYP2D6 genotype | | | |
|---|---|---|---|
| Genotype | N obs | LSMeans | P value |
| CC | 57 | 21.03 | |
| CT | 14 | 33.16 | <0.0001 |
| TT | 3 | 51.00 | |
| | TRT dose | | <0.0001 |
| | CYP2D6C100T *TRT dose | | 0.0015 |

This result is expected given the fact that this polymorphism is in almost complete linkage disequilibrium with the CYP2D6G1846A polymorphism.

In order to understand whether the difference in concentration of P88 at Period 1 Tmax was relevant to the increases in QTc after the addition of the inhibitors, the observed mean of P88 for the CYP2D6G1846A AG group was used to divide all individuals into two classes. The first includes individuals with P88 concentrations at Period 3, after the addition of both inhibitors, of equal to or less than 34 ng/mL and the second class includes individuals with P88 concentration greater than 34 ng/mL. The two classes were then compared in regards to the QTc change from baseline at Period 3. Using an ANOVA statistic for the first class P88>34 (n=55) the QTc mean change from baseline in Period 3 was 22.7 msec and that for P88<34 (n=12) the mean QTc for the same period was 7.7 msec. The QTc changes from baseline for Period 1 and Period 2 according to genotype and iloperidone dose are given in Table 6 and 7.

TABLE 6

QTc change at Period 1 according to CYP2D6 genotype and iloperidone dose

| | Iloperidone Dose | | |
|---|---|---|---|
| Genotype | 8 mg bid | 12 mg bid | 24 mg qd |
| | CYP2D6G1846A | | |
| AA | | 17.7 (1)[a] | 38.4 (1) |
| AG | −0.8 (3) | 5.8 (6) | 19.0 (5) |
| GG | 7.8 (17) | 11.8 (23) | 14.0 (14) |
| | CYP2D6C100T | | |
| TT | −8.4 (1) | 17.7 (1) | 38.4 (1) |
| CT | 2.9 (2) | 5.8 (6) | 19.0 (5) |
| CC | 7.8 (17) | 11.8 (23) | 9.5 (14) |

[a]number of individuals

TABLE 7

QTc change at Period 2 according to CYP2D6 genotype and iloperidone dose

| | Iloperidone Dose | | |
|---|---|---|---|
| Genotype | 8 mg bid | 12 mg bid | 24 mg qd |
| | CYP2D6G1846A | | |
| AA | | 25.0 (1) | 28.4 (1) |
| AG | 8.1 (3) | 8.7 (6) | 20.6 (5) |
| GG | 11.7 (18) | 14.5 (21) | 16.4 (15) |
| | CYP2D6C100T | | |
| TT | −0.7 (1) | 25.0 (1) | 28.4 (1) |
| CT | 12.5 (2) | 8.7 (6) | 20.6 (5) |
| CC | 11.7 (16) | 14.5 (21) | 16.4 (15) |

These results should be viewed with caution, however, since the number of observations is small. If one was to focus on the iloperidone 24 mg qd, there is a trend for higher QTc among AA, and AG individuals for CYP2D6G1846A as compared to GG. This difference disappears after the addition of the CYP2D6 inhibitor in Period 2.

These observations suggest that the differences in P88 concentrations during Period 1 between the different classes of genotypes may be relevant to QTc changes from baseline. Given the small number of observations and the unbalanced in regards to genotype design of the study, a confirmatory prospectively designed study may be required before any further interpretation of this data is warranted.

Notwithstanding these caveats, the results discussed above show that patients can be more safely treated with iloperidone if the dose of iloperidone is adjusted based on the CYP2D6 genotype of each patient. For example, if a patient has a genotype which results in decreased activity of the CYP2D6 protein relative to the wild type CYP2D6, then the dose of iloperidone administered to such patient would be reduced to, for example, 75% or less, 50% or less, or 25% or less of the dose typically administered to a patient having a CYP2D6 genotype that results in a CYP2D6 protein that has the same or substantially the same enzymatic activity on P88 as the wild type CYP2D6 genotype/protein. For example, where the normal dosage of iloperidone or other CYP2D6-metabolized compound administered to an individual is 24 mg per day, an individual with a genotype associated with decreased CYP2D6 activity may receive a reduced dosage of 18, 12, or 6 mg per day.

Decreased CYP2D6 activity may be the result of other mutations, including those described at www.imm.ki.se/CYPalleles/CYP2D6.htm, which is incorporated herein by reference. In particular, it is noted that the CYP2D6*2A mutation includes a CYP2D7 gene conversion in intron 1. In some cases, the lower CYP2D6 activity in a CYP2D6 poor metabolizer may be due to factors other than genotype. For example, a patient may be undergoing treatment with an agent, e.g., a drug that reduces CYP2D6 activity.

QTc prolongation is correlated to the ratios of P88/P95 and (iloperidone+P88)/P95. The mean ratios among CYP2D6 extensive metabolizers were 0.57 and 1.00, respectively. As shown above in Tables 3 and 5, CYP2D6 poor metabolizers have elevated P88 levels compared to CYP2D6 extensive metabolizers.

As CYP2D6 poor metabolizers comprise approximately 15% of the population, it was found that approximately 15% of those studied exhibited a P88/P95 ratio greater than 2.0 while the remaining 85% exhibited P88/P95 ratios less than 2.0. Table 8 below shows the least squares mean change in QTc for each dosage group. While the results for some groups are not statistically significant, they do indicate a trend supporting the hypothesis that QTc prolongation is correlated to P88/P95 ratio. Similar results were obtained when cutoff ratios of 3.0 and 4.0 were analyzed, providing further support to the hypothesis that the extent of QTc prolongation a patient may experience after treatment can be predicted by measuring P88 and P95 blood levels.

TABLE 8

Mean QTc Prolongation According to P88/P95 Ratio

| P88/P95 Ratio | LSMean QTc change from Baseline 8 mg bid | LSMean QTc change from Baseline 12 mg bid | LSMean QTc change from Baseline 8 + 12 mg bid | LSMean QTc change from Baseline 24 qd | LSMean QTc change from Baseline All Treatment Groups |
|---|---|---|---|---|---|
| <2 | 7.2 (n = 23) | 8.7 (n = 31) | 8.3 (n = 54) | 13.9 (n = 24) | 10.244 (n = 78) |
| >2 | 21.3 (n = 5) | 17.4 (n = 3) | 18.3 (n = 8) | 29.4 (n = 5) | 21.111 (n = 13) |
| P value | 0.0725 | 0.392 | 0.0815 | 0.0329 | 0.0131 |

Similar results were observed when considering QTc correlation to the (iloperidone+P88)/P95 ratio. Again, as approximately 15% of the population are CYP2D6 poor metabolizers, it was found that approximately 15% of those studied exhibited (iloperidone+P88)/P95 ratios greater than 3.0 while the remaining 85% exhibited ratios less than 3.0. Table 9 below shows the least squares mean change in QTc for each dosage group. While the results for some groups are not statistically significant, they do indicate a trend supporting the hypothesis that QTc prolongation is correlated to (iloperidone+P88)/P95 ratio. Indeed, when cutoff ratios of 3 and higher were analyzed, similar results were obtained providing further support to the hypothesis that the extent of QTc prolongation a patient may experience after treatment can be predicted by measuring iloperidone, P88 and P95 blood levels.

TABLE 9

| | Mean QTc Prolongation According to (iloperidone + P88)/P95 Ratio | | | | |
|---|---|---|---|---|---|
| (ILO + P88)/ P95 Ratio | LSMean QTc change from Baseline 8 mg bid | LSMean QTc change from Baseline 12 mg bid | LSMean QTc change from Baseline 8 + 12 mg bid | LSMean QTc change from Baseline 24 qd | LSMean QTc change from Baseline All Treatment Groups |
| <3 | 7.2 (n = 23) | 8.7 (n = 31) | 8.3 (n = 54) | 14.4 (n = 24) | 10.424 (n = 78) |
| >3 | 21.3 (n = 5) | 15.2 (n = 3) | 17.3 (n = 8) | 30.5 (n = 5) | 20.031 (n = 13) |
| P value | 0.0725 | 0.4223 | 0.0857 | 0.0522 | 0.0278 |

While the CYP2D6G1846A (AA or AG) genotype and the CYP2D6C100T (CT or TT) genotype are illustrated in this Example 1, the method of the invention can employ other genotypes that result in decreased activity of the CYP2D6 protein on iloperidone and P88. It is within the skill of the art, based on the disclosure herein, to identify additional CYP2D6 genotypes that result in decreased enzymatic activity on iloperidone and P88.

Example 2

A second study extended the pharmacogenomic assessment of iloperidone response by genotyping additional CYP2D6 variants which lead to the production of a non-functional protein or reduced enzymatic activity.

Six of the variants have been shown to result in the absence of a functional enzyme, either because of a deletion of the gene (as in the CYP2D6 *5 polymorphism), a frameshift (*3 and *6), a splicing error (*4), or a truncated or abnormal protein (*7 and *8). Five other polymorphisms were genotyped that resulted in the production of a functional protein that was shown to have a significantly decreased enzymatic activity on various compounds such as debrisoquine or sparteine (*9, *10, *17, *41), or only a modest reduction in activity (*2).

The actual impact of these individual polymorphisms on the enzyme vary from compound to compound, and the presence of several of them in the same protein can further reduce the CYP2D6 activity.

Methods

A. Samples

From the 300 iloperidone-treated patients initially genotyped for the CYP2D6*4 and *10 variants (VP-VYV-683-3101), 222 remaining DNA samples were used for this extended pharmacogenomic analysis. One patient was excluded from the analysis due to inconsistent results for the CYP2D6 allele *4 generated by Quest Diagnostics Central Laboratory (Collegeville, Pa.) and Cogenics (Morrisville, N.C.). Pharmacokinetic data of the (iloperidone+P88)/P95 ratio was available for 168 of these patients. QT measurement at Day 14 and 28 was available for 169 and 146 patients respectively.

B. Genotyping

Eleven specific CYP2D6 polymorphisms were evaluated (Table 10).

TABLE 10

| | CYP2D6 polymorphisms | | |
|---|---|---|---|
| Allele | DNA variations | Effect | Enzyme activity |
| *1 | Wild type | | Normal |
| *2 | 2850C > T; 4180G > C | R296C; S486T | Normal (dx, d, s) |
| *3 | 2549del | 259Frameshift | None (d, s) |
| *4 | 100C > T; 1661G > C; 1846G > A | P34S; splicing defect | None (d, s) |
| *5 | ***CYP2D6* deletion** | ***CYP2D6* deleted** | None (d, s) |
| *6 | 1707delT | 118Frameshift | None (d, s, dx) |
| *7 | 2935A > C | H324P | None (s) |
| *8 | 1661G > C; 1758G > T; 2850C > T; 4180G > C | G169X | None (d, s) |
| *9 | 2615_2617delAAG | K281del | Decreased (b, d, s) |
| *10 | 100C > T; 1661G > C; 4180G > C | P34S; S486T | Decreased (d, s) |
| *17 | 1023C > T; 1661G > C; 2850C > T; 4180G > C | T107I; R296C; S486T | Decreased (d) |
| *41 | −1584C; −1235A > G; −740C > T; −678G > A; CYP2D7 gene conversion in intron 1; 1661G > C; 2850C > T; 2988G > A; 4180G > C | R296C; splicing defect; S486T | Decreased (s) |

The DNA variations and their effects at the RNA or protein level listed here are based on the description by the Human Cytochrome P450 (CYP) Allele Nomenclature Committee available at: http://www.cypalleles.ki.se/CYP2D6.htm.
The in-vivo changes in enzyme activity have been reported for bufuralol (b), debrisoquine (d), dextromethorphan (dx), or sparteine (s).
The specific polymorphisms genotyped in the study reported here are shown in bold.

The genotypes of the CYP2D6*10 allele were generated by Quest Diagnostics Central Laboratory (Collegeville, Pa.); the genotypes of the CYP2D6 *2, *3, *5, *6, *7, *8, *9, *17 and *41 alleles were generated by Cogenics (Morrisville, N.C.); and the genotypes of the CYP2D6 *4 allele were obtained from Quest and also from Cogenics for a subset of patients.

The CYP2D6*2 allele is characterized by a series of mutations. In this assay, the cytosine to thymine transition at position 2850, which results in an arginine to cysteine substitution at amino acid 296, was tested (Johansson et al., 1993; Wang et al. 1995). The first round product from CYP2D6 multiplex PCR was amplified and the resulting product was digested with HhaI. The HhaI digestion resulted in 476, 372, 247, 178, and 84 basepair fragments for wt/wt genotype; 550, 476, 372, 247, 178, and 84 basepair fragments for *2/wt genotype; and 550, 476, 247, and 84 basepair fragments for *2/*2 genotype. The PCR products were gel electrophoresed and photographed under ultraviolet light.

The presence of the CYP2D6 alleles *3, *4, *6, *7, and *8 was assayed using multiplex PCR (Stuven et al. 1996). The CYP2D6 *3 allele results from a single base (adenine) deletion at nucleotide 2549 in exon 5 (Buchert et al., 1993). The defect in the CYP2D6 *4 allele is due to a guanine to adenine transition in the last nucleotide (position 1846) of intron 3 resulting in an aberrant 3' splice recognition site (Hanioka et al. 1990). The CYP2D6 *6 allele results from a thymine deletion at position 1707 in exon 3 resulting in a premature stop codon (Saxena et al. 1994). The CYP2D6 *7 allele results from an adenine to cytosine missense mutation at position 2935 which results in a histidine to proline substitution at amino acid 324 in exon 6 leading to a total loss of enzyme function (Evert et al. 1994). The defect in the CYP2D6 *8 allele is due to a guanine to thymine transition at position 1758 resulting in the insertion of a premature stop codon (Stuven et al. 1996).

The first round amplification generated a 1578 basepair product containing all five alleles. The 1578 basepair product served as the template for a multiplex allele-specific assay to simultaneously identify the five alleles. First round PCR template was added to two separate master mixes containing primers that recognize wild type or mutant alleles. These primers produce PCR products of 1394, 1010, 304, 219, and 167 basepairs for *7, *3, *4, *8, and *6 alleles, respectively. As an internal control, the primers for *8 were reversed; that is, the primer that recognizes the wild-type allele for *8 was present in the mutant master mix and the primer for the mutant allele for *8 was present in the wild-type master mix. For wild-type genotypes (except for *8), PCR products appeared in the wild-type lanes while no PCR products were observed in the mutant lane. For heterozygous genotypes, PCR products of the same fragment size appeared in both the wild-type and mutant lanes. For mutant genotypes (except for *8), PCR product appeared only in the mutant lane. The PCR products were gel electrophoresed and photographed under ultraviolet light.

The CYP2D6 *5 allele results from a complete deletion of the CYP2D6 gene (Gaedigk et al. 1991; Steen et al. 1995). A long-range PCR method was used to identify a deletion of the CYP2D6 locus. Presence or absence and intensity of PCR products identified the wild-type, heterozygous mutant, or mutant alleles. The PCR products were gel electrophoresed and photographed under ultraviolet light.

The CYP2D6 *9 mutation is a 3 basepair deletion at positions 2613-2615 (Tyndale et al. 1991). This results in a deletion of lysine at amino acid 281. The CYP2D6 *41 mutation is due to a guanine to adenine transition at position 2988 (Raimundo et al. 2004). The first round of amplification generated a 1578 basepair product containing the two alleles. The 1578 basepair product served as the template for a multiplex allele-specific assay to simultaneously identify the two alleles. First round PCR template was added to two separate master mixes containing primers that recognize wild-type or mutant alleles. These primers produced PCR products of 409, 593, and 780 basepairs for the *9 wild-type, internal control, and *41 wild-type, respectively. For wild-type genotypes, PCR products appeared in the wild-type lanes while no PCR products were observed in the mutant lane. For heterozygous genotypes, PCR products appeared in both the wild-type and mutant lanes. For mutant genotypes, PCR product appeared only in the mutant lane. The PCR products were gel electrophoresed and photographed under ultraviolet light.

The CYP2D6 *17 allele results from a cytosine to thymine base change at position 1023 which results in a threonine to isoleucine substitution at amino acid 107 in exon 2 (Masimirembwa et al. 1996). The first round of amplification generated a 369 basepair product containing the CYP2D6 *17 allele. The first round PCR template was added to two separate master mixes containing primers that recognize wild-type or mutant alleles as well as an internal control. These primers produced PCR products of 235 and 181 basepairs for the *17 allele and internal control, respectively. For a wild-type genotype, both PCR products appeared in the wild-type lanes while only the internal control PCR product was observed in the mutant lane. For heterozygous genotypes, both PCR products appeared in both the wild-type and mutant lanes. For a mutant genotype, both PCR products appeared in the mutant lanes while only the internal control PCR product is observed in the wild-type lane. The PCR products were gel electrophoresed and photographed under ultraviolet light.

C. Statistical Analysis

Analyses were performed on observed case data using an ANCOVA model with the baseline value as a covariate for the change from baseline in QTc (Fridericia formula) and using an ANOVA model for iloperidone blood exposure at Day 14 and Day 28. Linkage disequilibrium analysis was performed using Haploview v4.0 (Barrett et al, 2005).

Statistically significant associations were observed between the CYP2D6*4, CYP2D6*5, CYP2D6*10, and CYP2D6*41 alleles and the iloperidone blood exposure levels. The ratio of drug concentration [(iloperidone+P88)/P95] was increased with the presence of non-functional CYP2D6 alleles and of variants possibly associated with decreased enzymatic activity. Furthermore, patients who carried at least one non-functional CYP2D6 allele had a higher QTc prolongation after 14 days of iloperidone treatment than those with two functional copies. By Day 28, the QTcF prolongation was reduced but was still statistically different between the two patient groups.

The eleven CYP2D6 variants that were genotyped in iloperidone-treated patients are listed in Table 10, and their respective allele frequency per race is provided in Table 11.

TABLE 11

| CYP2D6 Allele Frequencies in Iloperidone-treated Patients | | | | | |
|---|---|---|---|---|---|
| Allele | Overall (N = 222) | Asian (N = 17) | Black & African Americans (N = 108) | White (N = 89) | Others (N = 8) |
| *2 | 39.2% (n = 174) | 32.3% (n = 11) | 44.4% (n = 96) | 34.3% (n = 61) | 37.5% (n = 6) |
| *4[†] | 12.7% (n = 75) | 12.0% (n = 6) | 11.0% (n = 33) | 16.2% (n = 35) | 3.8% (n = 1) |
| *5 | 5.2% (n = 23) | 2.9% (n = 1) | 6.0% (n = 13) | 4.5% (n = 8) | 6.3% (n = 1) |
| *6 | 0.4% (n = 2) | 0.0% (n = 0) | 0.5% (n = 1) | 0.5% (n = 1) | 0.0% (n = 0) |
| *7 | 0.2% (n = 1) | 2.9% (n = 1) | 0.0% (n = 0) | 0.0% (n = 0) | 0.0% (n = 0) |
| *8 | 0.0% (n = 0) | 0.0% (n = 0) | 0.0% (n = 0) | 0.0% (n = 0) | 0.0% (n = 0) |
| *9 | 1.8% (n = 8) | 0.0% (n = 0) | 0.5% (n = 1) | 3.9% (n = 7) | 0.0% (n = 0) |
| *10[†] | 16.0% (n = 95) | 20.0% (n = 10) | 14.7% (n = 44) | 17.1% (n = 37) | 15.4% (n = 4) |
| *17 | 9.5% (n = 42) | 5.9% (n = 2) | 17.6% (n = 38) | 1.1% (n = 2) | 0.0% (n = 0) |
| *41 | 5.9% (n = 26) | 8.8% (n = 3) | 1.4% (n = 3) | 11.2% (n = 20) | 0.0% (n = 0) |

[†]Genotypes for an additional 74 patients were obtained for markers *4 and *10, including 8 Asians, 42 Black and African Americans, 19 Whites, and 5 from other racial groups. N and n denote the number of patients and the number of alleles, respectively, from which frequencies were determined.

Six non-functional CYP2D6 variants were genotyped: *3, *4, *5, *6, *7, and *8. The most common variant was *4, detected in 16.2%, 11.0%, and 12.0% White, Black and African American, and Asian patients, respectively. It has been previously reported that the *4 variant was the most common non-functional CYP2D6 variant among Caucasians (~20%) and African Americans (7.5%), while it was expected to be rare among Asians (Bradford 2002). The *5 variant was observed at a frequency of 3-6%, depending on the racial group, consistent with previous reports (Bradford 2002). As expected, *3, *6, *7 were rare, and *8 was not observed in any patient.

Four variants were genotyped which are associated with reduced CYP2D6 enzymatic activity: *10 has been observed frequently in Asia (38-70%), *17 has been reported in ~22% of African Americans, *41 is believed to be common among Caucasians (possibly ~20%), and *9 has been observed only in a small percentage of individuals (1-2%) (Bradford 2002).

The *10 variant was observed in 15-20% of the iloperidone-treated patients across all racial groups. *10 occurred more frequently than expected for Whites and African Americans, but less frequently among Asians. Other studies have reported a high percentage of *10 in Asians (all above 38%) but a much lower percentage in Caucasians (4-8%) and in African Americans (2-7%) (Bradford 2002). Variant *17 was the most common variant in Black and African Americans (17.6%), and more rare in Asians (5.9%) and Whites (1.1%); this result is in agreement with the expected frequencies for these populations (Bradford 2002).

As expected, the *41 variant was most common amongst Whites (11.2%) and rare in African Americans (1.4%). This variant, which has not been extensively studied in other populations, was also seen in 8.8% of Asians.

The functional *2 variant has been reported as the most commonly occurring variant coding for a CYP2D6 protein, with a slightly reduced activity (~80% of the wild type) (Bradford 2002). The *2 variant was the most commonly observed variant, with a frequency of 32 to 44% depending of the racial group.

Because of the high frequency of the CYP2D6 variants, it is likely that a number of individuals carry more than one allele associated with reduced or abolished enzymatic activity.

Only 7 patients (3.1%) with 2 non-functional alleles were identified in this study: 6 homozygotes *4/*4 and one compound heterozygote *5/*4. Seventy-two patients (32.1%) had only one functional copy of CYP2D6. Sixty-one patients (27.2%) had 2 functional copies of CYP2D6, with one or 2 allelic variants with possible decreased enzymatic activity. The other 84 patients (37.5%) carried only the *2 variant or were homozygote wt/wt at each variant locus. Linkage Disequilibrium (LD) analysis revealed that several CYP2D6 loci were in complete linkage disequilibrium. The *4 variant was in LD with *10 (D'=1, LD 42.33) and *2 (D'=1, LD 5.75). The *2 variant was also in LD with *17 (D'=1, LD 13.44), *10 (D'=1, LD 8.89), and *41 (D'=1, LD 5.43).

Analysis of individual CYP2D6 variants with iloperidone blood exposure showed that the *4 and *10 variants were significantly associated with the (iloperidone+P88)/P95 ratio, with ratios of 2.28 for the *4 allele as compared to 1.10 for the wt (p=2.8E-08) and 2.20 for the *10 allele as compared to 1.03 for the wt (p=2.4E-09) (Table 12). Significant association was also seen for the *5 and *41 variants with ratios of 2.16 for the *5 allele as compared to 1.19 for the wt (p=0.0016) and 2.02 for the *41 allele as compared to 1.19 for the wt (p=0.0045) (Table 12).

TABLE 12

Association of CYP2D6 Alleles With Exposure to Iloperidone at Day 14

| Variant | Allele | N | Mean (Iloperidone + P88)/P95 Ratio | P value |
|---|---|---|---|---|
| CYP2D6*2 | *2 | 104 | 1.37 | 0.45 |
| | wt | 60 | 1.21 | |
| CYP2D6*4 | *4 | 53 | 2.28 | 2.8E-08 |
| | wt | 165 | 1.10 | |

TABLE 12-continued

Association of CYP2D6 Alleles With Exposure to Iloperidone at Day 14

| Variant | Allele | N | Mean (Iloperidone + P88)/P95 Ratio | P value |
|---|---|---|---|---|
| CYP2D6*5 | *5 | 20 | 2.16 | 0.0016 |
| | wt | 144 | 1.19 | |
| CYP2D6*7 | *7 | 1 | 1.97 | 0.61 |
| | wt | 163 | 1.30 | |
| CYP2D6*9 | *9 | 8 | 1.33 | 0.96 |
| | wt | 156 | 1.3 | |
| CYP2D6 | *10 | 67 | 2.20 | 2.4E-09 |
| *10 | wt | 151 | 1.03 | |
| CYP2D6 | *17 | 28 | 0.93 | 0.090 |
| *17 | wt | 136 | 1.39 | |
| CYP2D6 | *41 | 23 | 2.02 | 0.0045 |
| *41 | wt | 141 | 1.19 | |

As discussed previously, the presence of multiple CYP2D6 variants may further affect the overall amount of CYP2D6 expressed and its total enzymatic activity. Therefore, an additional analysis was conducted, taking into account the presence of all functional and non-functional alleles as well as the expected decreased activity associated with some of the variants. A clear gradient of increased (iloperidone+P88)/P95 ratio was observed with the presence of alleles associated with decreased activity and non-functional alleles (Table 13). Patients with 2 non-functional alleles were found to have an (iloperidone+P88)/P95 ratio of 6.4, which was much higher than patients with only one non-functional allele (1.8), with one or two alleles associated with decreased activity (1.15), or with two functional alleles (0.80) (Table 13).

TABLE 13

Effect of CYP2D6 Variants on Iloperidone Blood Exposure at Day 14

| Combination of 2 CYP2D6 alleles | N | Mean (Iloperidone + P88)/P95 Ratio | P value |
|---|---|---|---|
| 2 functional alleles (*1 or *2) | 60 | 0.80 | |
| 2 functional alleles with 1 or 2 alleles associated with decreased activity | 49 | 1.15 | 0.018 |
| 1 non-functional allele, and 1 functional allele associated or not with decreased activity | 54 | 1.80 | 1.1E-07 |
| 2 non-functional alleles | 5 | 6.40 | 3.1E-17 |

Since a significantly decreased metabolism of iloperidone was observed in patients who carried at least one non-functional CYP2D6 allele, whether or not these patients had also an increased QTcF prolongation after iloperidone treatment (Table 14) was also investigated. After 14 days of treatment, patients with at least one non-functional CYP2D6 allele had a significantly higher prolongation of the QTcF interval (16.3 msec) than those with 2 functional copies (9.7 msec, p=0.01). By Day 28, the QTcF prolongation was reduced but was still statistically different between the 2 groups (11.4 and 4.4 msec respectively, p=0.02).

TABLE 14

| Effect of CYP2D6 Variants on QTcF prolongation | | | | |
|---|---|---|---|---|
| | Day 14 | | Day 28 | |
| CYP2D6 alleles | QTcF change (msec) [†] | Mean (Iloperidone + P88)/P95 Ratio | QTcF change (msec) [†] | Mean (Iloperidone + P88)/P95 Ratio |
| 2 functional alleles | 9.7 (N = 110) | 1.0 (N = 109) | 4.4 (N = 90) | 0.8 (N = 103) |
| 1 or 2 non-functional alleles | 16.3 (N = 59) | 2.2 (N = 59) | 11.4 (N = 56) | 2.4 (N = 59) |
| | P = 0.01 | P = 6.8E–08 | P = 0.02 | P = 1.4 E–07 |

[†] LS Squares Mean QTcF change from baseline

D. Results and Discussion

Comparison based on the (iloperidone+P88)/P95 ratio regardless of the specific CYP2D6 genotype revealed that patients with a ratio ≤1 have a QTc at Day 14 of 7.9 msec as compared to 16.0 msec for patients with a ratio >1, p=0.0002 (Table 15). At Day 28, QTcF was reduced to 4.8 and 10.1 msec for patients with a ratio ≤1 or >1 respectively.

TABLE 15

| Effect of Iloperidone Blood Exposure on QTcF prolongation | | |
|---|---|---|
| Mean (Iloperidone + P88)/P95 Ratio | Day 14 QTcF change (msec) [†] | Day 28 QTcF change (msec) [†] |
| ≤1 | 7.9 (N = 127) | 4.8 (N = 119) |
| >1 | 16.0 (N = 99) | 10.1 (N = 79) |
| | P = 0.0002 | P = 0.062 |

[†] LS Squares Mean QTcF change from baseline

The genotyping of multiple CYP2D6 variants in more than 200 iloperidone-treated patients (Table 11) revealed that the CYP2D6*4 and *10 alleles, which are in linkage disequilibrium, were the most common alleles associated with decreased or abolished enzymatic activity in Whites (16.2 and 17.1% respectively ) and Asians (12 and 20% respectively). In Black and African Americans, the *17 allele was more common than the *4 and *10 alleles (17.6% vs. 11 and 14.7% respectively). The frequency of the *5 allele was ~5%, while the other non-functional alleles were very rare. Most extensive analyses of frequency data of CYP2D6 variants came from European Caucasians populations, Chinese and Japanese populations, or selected African regions. To date, few studies have been reported on allele frequencies in the US population, and some of the differences observed in this study with data from European Caucasians, Africans, Chinese or Japanese populations are likely to reflect regional and national specificities of US populations.

It was observed that the *4, *10, *5 and *41 alleles were significantly associated with a reduced CYP2D6 iloperidone metabolism, more specifically, an increase of the (iloperidone+P88)/P95 ratio (Table 12). When taking into account the genotype data of all alleles tested, this ratio was shown to be clearly dependent on the number of non-functional alleles and of alleles associated with decreased activity (Table 13).

Furthermore it appears that the reduced iloperidone metabolism was associated with a higher QTcF prolongation after 14 and 28 days of treatment. A significant difference was observed between patients with at least one-functional CYP2D6 allele and patients with 2 functional alleles (Table 14). This difference was also observed between patients with a (iloperidone+P88)/P95 ratio ≤1 or >1 regardless of their specific CYP2D6 genotypes (Table 15). These results offer a potential risk management strategy and prospective testing tools for physicians when treating patients with iloperidone if the potential for QTcF prolongation is considered to be a risk for the patient.

The starting point for determining the optimum dose of iloperidone is, as discussed above, a dose that has been shown to be acceptably safe and effective in patients having a CYP2D6 genotype that results in a protein having the same activity on iloperidone and P88 as the wild type CYP2D6 protein. Such doses are known in the art and are disclosed, for example, in U.S. Pat. No. 5,364,866 discussed above.

Generally, the dose of iloperidone administered to a patient will be decreased, as discussed above, if the enzymatic activity of the CYP2D6 enzyme on iloperidone and P88 is less than about 75% of that of the wild type CYP2D6. Enzymatic activity may be determined by any number of methods, including, for example, measuring the levels of iloperidone and/or P88 in an individual's blood. In such a case, the iloperidone dose can be lowered such that measured levels of iloperidone and/or P88 are substantially the same as levels measured in the blood of individuals having normal CYP2D6 enzymatic activity. For example, if the CYP2D6 enzymatic activity of a patient is estimated by one or more methods (e.g., genotyping, determination of dextromorphan blood levels) to be 50% of the enzymatic activity normally observed in an individual having normal CYP2D6 enzymatic activity, the dose for the patient may need to be adjusted to one-half of the dose given to an individual having normal CYP2D6 enzymatic activity. Similarly, for ultrarapid metabolizers, an analogous calculation will lead to the conclusion that a dose adjustment of twice that given an individual having normal CYP2D6 enzymatic activity may be needed in order to achieve similar blood levels for the parent compound and active metabolites.

Alternatively, the dose of iloperidone administered to a patient may be decreased based upon the patient's CYP2D6 genotype alone, or upon the patient's P88:P95 or (iloperidone+P88):P95 ratios. For example, if a patient has a "poor metabolizer" genotype, or has a high P88:P95 or (iloperidone+P88):P95 ratio, the patient's dose of iloperidone may be reduced by, for example, 25%, 50%, or 75%. A patient's genotype can be readily determined using standard techniques on samples of body fluids or tissue. Such techniques are disclosed, e.g., in PCT Application Publication Number WO03054226.

Furthermore, while the disclosure herein focuses on genotype, it is apparent to one of skill in the art that phenotype can also be used as an indicator of decreased activity of the CYP2D6 protein on iloperidone and P88. For example, McElroy et al. describe a correlation between CYP2D6 phenotype and genotyping as determined by dextromethorphan/dextrorphan ratios. Therefore, although it is more convenient given the state of the art to look at genotype, if one were to determine that a given patient expressed a mutant CYP2D6 with lower activity on iloperidone and P88 than the wild type, or expressed abnormally low amounts of CYP2D6, then that patient would be given a lower dose of iloperidone than a patient with wild type CYP2D6, as discussed above. Alternative methods for determining the relative activity of a patient's CYP2D6 gene include biochemical assays to directly measure enzymatic activity, protein sequencing to examine the amino acid sequence of a patient's CYP2D6, monitoring transcription and translation levels, and sequencing the CYP2D6 gene mRNA transcript. For example, Chainuvati et al. describe assessment of the CYP2D6 phenotype using a multi-drug phenotyping cocktail (the Cooperstown 5+1 cocktail).

Iloperidone can be formulated into dosage units and administered to patients using techniques known in the art. See, e.g., PCT Application Publication Number WO03054226, US Patent Application Publication Number 20030091645, PCT Application Serial Number PCT EP03/07619, and PCT Application Publication Number WO02064141, all of which are incorporated herein by reference as though fully set forth.

In addition, the present invention provides a kit for determining a patient's CYP2D6 genotype and/or phenotype. Such a kit may include, for example, a detection means, a collection device, containers, and instructions, and may be used in determining a treatment strategy for a patient having one or more diseases or disorders for which iloperidone treatment is indicated.

Detection means may detect a CYP2D6 polymorphism directly or may detect the characteristic mRNA of the polymorphic gene or its polypeptide expression product. In addition, as will be recognized by one of skill in the art, detection means may also detect polymorphisms in linkage disequilibrium with a CYP2D6 polymorphism. Accordingly, any polymorphism in linkage disequilibrium with the CYP2D6 polymorphisms disclosed in this application may be used to indirectly detect such a CYP2D6 polymorphism, and is within the scope of the present invention.

Detection means suitable for use in the methods and devices of the present invention include those known in the art, such as polynucleotides used in amplification, sequencing, and single nucleotide polymorphism (SNP) detection techniques, Invader® assays (Third Wave Technologies, Inc.), Taqman® assays (Applied Biosystems, Inc.), gene chip assays (such as those available from Affymetrix, Inc. and Roche Diagnostics), pyrosequencing, fluorescence resonance energy transfer (FRET)-based cleavage assays, fluorescent polarization, denaturing high performance liquid chromatography (DHPLC), mass spectrometry, and polynucleotides having fluorescent or radiological tags used in amplification and sequencing.

A preferred embodiment of a kit of the present invention includes an Invader® assay, wherein a specific upstream "invader" oligonucleotide and a partially overlapping downstream probe together form a specific structure when bound to a complementary DNA sequence. This structure is recognized and cut at a specific site by the Cleavase enzyme, releasing the 5' flap of the probe oligonucleotide. This fragment then serves as the "invader" oligonucleotide with respect to synthetic secondary targets and secondary fluorescently-labeled signal probes contained in a reaction mixture. This results in the specific cleavage of the secondary signal probes by the Cleavase enzyme. Fluorescence signal is generated when this secondary probe, labeled with dye molecules capable of fluorescence resonance energy transfer, is cleaved. Cleavases have stringent requirements relative to the structure formed by the overlapping DNA sequences or flaps and can, therefore, be used to specifically detect single base pair mismatches immediately upstream of the cleavage site on the downstream DNA strand. See, e.g., Ryan et al., Molecular Diagnosis, 4; 2:135-144 (1999); Lyamichev et al., Nature Biotechnology, 17:292-296 (1999); and U.S. Pat. Nos. 5,846,717 and 6,001,567, both to Brow et al., all of which are hereby incorporated herein by reference.

Another preferred embodiment of a kit of the present invention includes a detection means comprising at least one CYP2D6 genotyping oligonucleotide specific to alleles known to predict a patient's metabolizer phenotype. More particularly, the means comprises an oligonucleotide specific for the CYP2D6G1846A or CYP2D6C100T polymorphism. The means may similarly comprise oligonucleotides specific for each polymorphism as well as the wild type sequence.

Detection methods, means, and kits suitable for use in the present invention are described in International Publication Nos. WO 03/0544266 and WO 03/038123, each of which is hereby incorporated herein by reference. It should also be understood that the methods of the present invention described herein generally may further comprise the use of a kit according to the present invention.

Collection devices suitable for use in the present invention include devices known in the art for collecting and/or storing a biological sample of an individual from which nucleic acids and/or polypeptides can be isolated. Such biological samples include, for example, whole blood, semen, saliva, tears, urine, fecal material, sweat, buccal smears, skin, hair, and biopsy samples of organs and muscle. Accordingly, suitable collection devices include, for example, specimen cups, swabs, glass slides, test tubes, lancets, and Vacutainer® tubes and kits.

The present invention encompasses treatment of a patient for any disease or condition that is ameliorated by administration of iloperidone. As discussed above, such diseases or conditions include, for example, schizoaffective disorders including schizophrenia, depression including bipolar depression, as well as other conditions such as cardiac arrythmias, Tourette's syndrome, psychotic disorders and delusional disorders.

A related aspect of the invention is a method for obtaining regulatory approval for a pharmaceutical composition comprising iloperidone or an active metabolite thereof, or a pharmaceutically acceptable salt of either, which comprises including in proposed prescribing information instructions to determine whether or not a patient is a CYP2D6 poor metabolizer prior to determining what dose to administer to the patient. In another related aspect, the invention is a method for commercializing (i.e., selling and promoting) pharmaceutical compositions comprising such compounds said method comprising obtaining regulatory approval of the composition by providing data to a regulatory agency demonstrating that the composition is effective in treating humans when administered in accordance with instructions to determine whether or not a patient is a CYP2D6 poor metabolizer prior to determining what dose to administer to the patient and then disseminating information concerning the use of such composition in such manner to prescribers (e.g., physicians) or patients or both.

Another aspect of the invention is a method for obtaining regulatory approval for the administration of iloperidone based, in part, on labeling that instructs the administration of a lower dose if the patient is already being administered a CYP2D6 inhibitor, e.g., paroxetine, etc.

Embodiments

1. A method for treating a patient with an active pharmaceutical ingredient including at least one of: iloperidone, a pharmaceutically acceptable salt of iloperidone, an active metabolite of iloperidone, and a pharmaceutically acceptable salt of an active metabolite of iloperidone, comprising the steps of: determining the patient's CYP2D6 genotype; and administering to the patient an effective amount of the active pharmaceutical ingredient, whereby the amount of the active pharmaceutical ingredient is determined based on the patient's CYP2D6 genotype.

2. The method of embodiment 1, wherein the amount of the active pharmaceutical ingredient is decreased if the genotype indicates decreased enzymatic activity of the CYP2D6 enzyme relative to the wild type.

3. The method of embodiment 2, wherein the amount of the active pharmaceutical ingredient is decreased if the patient's CYP2D6G1846A genotype is AA.

4. The method of embodiment 2, wherein the amount of the active pharmaceutical ingredient is decreased if the patient's CYP2D6G1846A genotype is GA.

5. The method of embodiment 2, wherein the amount of the active pharmaceutical ingredient is decreased if the patient's CYP2D6C100T genotype is TT.

6. The method of embodiment 2, wherein the amount of the active pharmaceutical ingredient is decreased if the patient's CYP2D6C100T genotype is CT.

7. The method of embodiment 2, wherein the amount of the active pharmaceutical ingredient is decreased if the patient's CYP2D6 genotype is 100C>T; 1661G>C; 1846G>A.

8. The method of embodiment 2, wherein the amount of the active pharmaceutical ingredient is decreased if the patient's CYPD26 genotype is 100C>T; 1661G>C; 4180G>C.

9. The method of embodiment 2, wherein the amount of the active pharmaceutical ingredient is decreased if the patient's CYP2D6 genotype is CYP2D6 deleted.

10. The method of embodiment 2, wherein the amount of the active pharmaceutical ingredient is decreased if the patient's CYP2D6 genotype is −1584C; −1235 A>G; −740 C>T; 678 G>A; CYP2D7 gene conversion in intron 1; 1661 G>C; 2850 C>T; 2988 G>A; 4180 G>C.

11. The method of embodiment 1, wherein the patient is suffering from at least one of schizophrenia, schizoaffective disorder, depression, bipolar mania/depression, cardiac arrhythmia, Tourette's Syndrome, a psychotic disorder, a delusional disorder, and schizophreniform disorder.

12. The method of embodiment 11, wherein the patient is at risk for a prolonged QT interval.

13. A method for treating a patient who is a CYP2D6 poor metabolizer with a pharmaceutically active ingredient including at least one of: iloperidone, a pharmaceutically acceptable salt of iloperidone, an active metabolite of iloperidone, and a pharmaceutically acceptable salt of an active metabolite of iloperidone, wherein the patient is administered a lower dosage than would be given to an individual who is not a CYP2D6 poor metabolizer.

14. The method of embodiment 13, wherein the patient is determined to be a CYP2D6 poor metabolizer based on at least one of the patient's genotype, the patient's phenotype, and the fact that the patient is being treated with an agent that reduces CYP2D6 activity.

15. The method of embodiment 13, wherein the patient's genotype includes at least one CYP2D6 allele selected from a group consisting of 2549 A deletion, 1846 G>A, 1707 T deletion, 2935 A>C, 1758 G>T, 2613-2615 AGA deletion, 1023 C>T, 2850 C>T, 4180G>C, 1659 G>A, 1661 G>C, 2850 C>T, 3183 G>A, −1584 C, −1235 A>G, −740C>T, −678 G>A, 100 C>T, 2988 G>A, and CYP2D6 deletion.

16. The method of embodiment 14, wherein the patient's genotype includes at least one deletion of the CYP2D6 gene.

17. The method of embodiment 15, wherein the patient's genotype includes a CYP2D7gene conversion in intron 1.

18. The method of embodiment 13, wherein the patient is suffering from at least one of schizophrenia, schizoaffective disorder, depression, bipolar mania/depression, cardiac arrhythmia, Tourette's Syndrome, a psychotic disorder, a delusional disorder, and schizophreniform disorder.

19. A method of treating a patient with a pharmaceutically active ingredient including at least one of: iloperidone, a pharmaceutically acceptable salt of iloperidone, an active metabolite of iloperidone, and a pharmaceutically acceptable salt of an active metabolite of iloperidone comprising the steps of: determining whether the patient is being administered a CYP2D6 inhibitor; and reducing the dosage of drug if the patient is being administered a CYP2D6 inhibitor.

20. The method of embodiment 19, wherein the CYP2D6 inhibitor includes at least one of paroxetine, dolasetron, venlafaxin, and fluoxetine.

21. The method of embodiment 19, wherein the patient is suffering from at least one of schizophrenia, schizoaffective disorder, depression, bipolar mania/depression, cardiac arrhythmia, Tourette's Syndrome, a psychotic disorder, a delusional disorder, and schizophreniform disorder.

22. A method for determining a patient's CYP2D6 phenotype comprising the steps of: administering to the patient a quantity of at least one of: iloperidone, a pharmaceutically acceptable salt of iloperidone, an active metabolite of iloperidone, and a pharmaceutically acceptable salt of an active metabolite of iloperidone; and determining a first concentration of at least one of iloperidone and an iloperidone metabolite in the patient's blood.

23. The method of embodiment 22, wherein the iloperidone metabolite is selected from a group consisting of P88 and P95.

24. The method of embodiment 23, wherein a first concentration is determined for each of P88 and P95.

25. The method of embodiment 24, wherein the patient is designated a poor metabolizer if the ratio of first concentrations of P88 to P95 is greater than or equal to about 2.0.

26. The method of embodiment 24, wherein the patient is designated a poor metabolizer if the ratio of first concentrations of (P88+iloperidone)/P95 is greater than or equal to about 1.0.

27. The method of embodiment 24, wherein the patient is designated a poor metabolizer if the ratio of first concentrations of iloperidone and P88 to P95 is greater than or equal to about 3.0.

28. The method of embodiment 22, further comprising the steps of: administering to the patient at least one CYP2D6 inhibitor; determining a second concentration of at least one of iloperidone and an iloperidone metabolite in the patient's blood; and comparing the first and second concentrations.

29. The method of embodiment 28, wherein the CYP2D6 inhibitor is selected from a group consisting of paroxetine, ketoconazole, and fluoxetine.

30. The method of embodiment 28, wherein a second concentration is determined for each of P88 and P95.

31. The method of embodiment 30, wherein the patient is designated a poor metabolizer if the ratio of second concentrations of P88 to P95 is greater than or equal to about 2.0.

32. The method of embodiment 28, wherein a first and second concentration is determined for each of iloperidone, P88, and P95.

33. The method of embodiment 32, wherein the patient is designated a poor metabolizer if the ratio of second concentrations of iloperidone and P88 to P95 is greater than or equal to about 3.0.

34. A method for determining whether a patient is at risk for prolongation of his or her QTc interval due to administration of at least one of: iloperidone, a pharmaceutically acceptable salt of iloperidone, an active metabolite of iloperidone, and a pharmaceutically acceptable salt of an active metabolite of iloperidone comprising the steps of: measuring a first QTc interval; administering to the patient a quantity of at least one of: iloperidone, a pharmaceutically acceptable salt of iloperidone, an active metabolite of iloperidone, and a pharmaceutically acceptable salt of an active metabolite of iloperidone, measuring a second QTc interval; and comparing the first and second QTc interval.

35. The method of embodiment 34, wherein the dose of iloperidone administered to the patient is about 24 milligrams per day.

36. The method of embodiment 34, further comprising the step of administering to the patient at least one CYP2D6 inhibitor after the administering step.

37. The method of embodiment 36, wherein the CYP2D6 inhibitor is selected from a group consisting of paroxetine, ketoconazole, and fluoxetine.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A method for treating a patient with a compound that is iloperidone or a metabolite thereof, wherein the patient is suffering from schizophrenia, the method comprising the steps of:
   determining that the patient demonstrates reduced CYP2D6-mediated metabolism relative to wild type by:
      obtaining or having obtained a biological sample from the patient;
      performing or having performed a genotyping assay on the biological sample; and
      determining that the patient has a genotype associated with reduced CYP2D6-mediated metabolism, wherein the genotype includes two CYP2D6*41 alleles; and
   administering the compound to the patient in a first amount that is one of 25%, 50%, or 75% of a second amount of 24 mg/day, that would be administered to a patient demonstrating CYP2D6-mediated metabolism consistent with a wild type CYP2D6 genotype, and
   wherein a risk of QTc prolongation for the patient is lower following the administration of the first amount of the compound than it would be if the compound were administered in the second amount.

2. The method of claim 1, wherein the performing or having performed the genotyping assay step comprises:
   extracting or having extracted genomic DNA or mRNA from the biological sample, and
   sequencing or having sequenced CYP2D6 DNA derived from the extracted genomic DNA or from the extracted mRNA,
   wherein the sequencing or having sequenced step further comprises:
   amplifying or having amplified a CYP2D6 region in the extracted genomic DNA or mRNA to prepare a DNA sample enriched in DNA from the CYP2D6 gene region; and
   sequencing or having sequenced the DNA sample by hybridizing the DNA sample to nucleic acid probes to determine if the patient has the genotype including two CYP2D6*41 alleles.

3. The method of claim 1, wherein the first amount of the compound is about 12 mg/day.

4. A method of treating a patient who is suffering from a schizoaffective disorder, depression, Tourette's syndrome, a psychotic disorder or a delusional disorder, the method comprising:
   determining that the patient has a genotype associated with reduced CYP2D6-mediated metabolism by:
      obtaining or having obtained a biological sample from the patient, and
      performing or having performed a genotyping assay on the biological sample to determine that the patient has a genotype associated with reduced CYP2D6-mediated metabolism, wherein the genotype includes two CYP2D6 *41 alleles; and
   administering a compound that is iloperidone or a metabolite thereof to the patient in a first amount,
   wherein the first amount of the compound is 25%, 50%, or 75% of a second amount of 24 mg/day of the compound that would be administered to a patient demonstrating CYP2D6-mediated metabolism consistent with a wild type CYP2D6 genotype,
   wherein a risk of QTc prolongation for the patient is lower following the administration of the first amount of the compound than it would be if the compound were administered in the second amount.

5. The method of claim 4, wherein the patient is at risk for a prolonged QT interval.

6. The method of claim 4, wherein the first amount of the compound is about 12 mg/day.

7. A method of treating a patient who is suffering from a schizoaffective disorder, depression, Tourette's syndrome, a psychotic disorder or a delusional disorder, the method comprising:
   determining that the patient is at risk for iloperidone-induced QTc prolongation by:
      obtaining or having obtained a biological sample from the patient, and
      performing or having performed a genotyping assay on the biological sample to determine whether the patient has a CYP2D6 poor metabolizer genotype that includes two CYP2D6 *41 alleles, wherein the presence of the CYP2D6 poor metabolizer genotype indicates risk for iloperidone-induced QTc prolongation, and administering a compound that is or a metabolite thereof, to the patient in a first amount, wherein the first amount of the compound is one of 25%, 50%, or 75% of a second amount of 24 mg/day of the compound, wherein the second amount causes an iloperidone blood exposure level that is therapeutically effective in a patient not having a CYP2D6 poor metabolizer genotype.

8. The method of claim 7, wherein the patient is at risk for iloperidone-induced QTc prolongation.

9. The method of claim 7, wherein the first amount of iloperidone is about 12 mg/day.

10. The method of claim 1, wherein the compound comprises the metabolite of iloperidone, the metabolite being (1-[4-[3-[4-(6-fluoro-1,2-benzisoxazol-3-yl)-1-piperidinyl] propoxy]-3-methoxyphenyl] ethanol) (P88).

11. The method of claim 1, wherein the first amount of the compound is about 6 mg/day.

12. The method of claim 1, wherein the first amount of the compound is about 18 mg/day.

13. The method of claim 4, wherein the compound comprises the metabolite of iloperidone, the metabolite being (1-[4-[3-[4-(6-fluoro-1,2-benzisoxazol-3-yl)-1-piperidinyl] propoxy]-3-methoxyphenyl] ethanol) (P88).

14. The method of claim 4, wherein the first amount of the compound is about 6 mg/day.

15. The method of claim 4, wherein the first amount of the compound is about 18 mg/day.

16. The method of claim 7, wherein the compound comprises the metabolite of iloperidone, the metabolite being (1-[4-[3-[4-(6-fluoro-1,2-benzisoxazol-3-yl)-1-piperidinyl] propoxy]-3-methoxyphenyl] ethanol) (P88).

17. The method of claim 7, wherein the first amount of the compound is about 6 mg/day.

18. The method of claim 7, wherein the first amount of the compound is about 18 mg/day.

19. The method of claim 1, wherein the first amount of the compound is administered in twice daily (bid) divided doses.

20. The method of claim 4, wherein the first amount of the compound is administered in twice daily (bid) divided doses.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Primer for amplifying CYP2D6 Exons 1 and 2

<400> SEQUENCE: 1
ctgggctggg agcagcctc                                                  19

<210> SEQ ID NO 2
<211> LENGTH: 23
<212> TYPE: DNA
<213> ORGANISM: Artificial Sequence
<220> FEATURE:
<223> OTHER INFORMATION: Primer for amplifying CYP2D6 Exons 1 and 2

<400> SEQUENCE: 2
cactcgctgg cctgtttcat gtc                                             23

<210> SEQ ID NO 3
<211> LENGTH: 22
<212> TYPE: DNA
<213> ORGANISM: Artificial Sequence
<220> FEATURE:
<223> OTHER INFORMATION: Primer for amplifying CYP2D6 Exons 3, 4, 5 and
      6

<400> SEQUENCE: 3
ctggaatccg gtgtcgaagt gg                                              22

<210> SEQ ID NO 4
<211> LENGTH: 20
<212> TYPE: DNA
<213> ORGANISM: Artificial Sequence
<220> FEATURE:
<223> OTHER INFORMATION: Primer for amplifying CYP2D6 Exons 3, 4, 5 and
      6

<400> SEQUENCE: 4
ctcggcccct gcactgtttc                                                 20
```

-continued

```
<210> SEQ ID NO 5
<211> LENGTH: 22
<212> TYPE: DNA
<213> ORGANISM: Artificial Sequence
<220> FEATURE:
<223> OTHER INFORMATION: Primer for amplifying CYP2D6 Exons 7, 8 and 9

<400> SEQUENCE: 5
gaggcaagaa ggagtgtcag gg                                                    22

<210> SEQ ID NO 6
<211> LENGTH: 23
<212> TYPE: DNA
<213> ORGANISM: Artificial Sequence
<220> FEATURE:
<223> OTHER INFORMATION: Primer for amplifying CYP2D6 Exons 7, 8 and 9

<400> SEQUENCE: 6
agtcctgtgg tgaggtgacg agg                                                   23
```